United States Patent
Hagemann

Patent Number: 5,426,022
Date of Patent: Jun. 20, 1995

[54] PHOTOGRAPHIC RECORDING MATERIAL COMPRISING A SPECIFIC LIGHT STABILIZING COMPOUND

[75] Inventor: Jörg Hagemann, Köln, Germany

[73] Assignee: Agfa-Gevaert AG, Leverkusen, Germany

[21] Appl. No.: 270,446

[22] Filed: Jul. 5, 1994

[30] Foreign Application Priority Data

Jul. 14, 1993 [DE] Germany .......... 43 23 477.1

[51] Int. Cl.⁶ .......... G03C 1/08; G03C 7/26; G03C 7/32
[52] U.S. Cl. .......... 430/551; 430/554; 430/555; 430/556; 430/557; 430/558
[58] Field of Search .......... 430/551, 372, 554, 555, 430/558, 556, 557

[56] References Cited
U.S. PATENT DOCUMENTS
4,732,845  3/1988  Keiji et al. .......... 430/551

Primary Examiner—Charles L. Bowers, Jr.
Assistant Examiner—Geraldine Letscher
Attorney, Agent, or Firm—Connolly & Hutz

[57] ABSTRACT

Compounds of Formula I are suitable as light stabilizers for the image dyes produced during chromogenic development from magenta couplers or yellow couplers

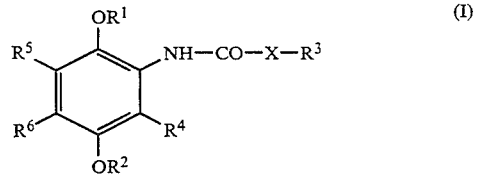

In Formula I:
$R^1$, $R^2$, $R^3$ signify alkyl, aryl;
$R^4$, $R^5$, $R^6$ signify H, alkyl, alkoxy, aryloxy, acyloxy,

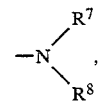

alkoxycarbonyl, carbamoyl;
$R^7$ signifies H, alkyl, aryl;
$R^8$ signifies alkyl, aryl, acyl;
X signifies a single bond, —O—, —NH—.

10 Claims, No Drawings

PHOTOGRAPHIC RECORDING MATERIAL COMPRISING A SPECIFIC LIGHT STABILIZING COMPOUND

The invention relates to a photographic recording material with at least one silver halide emulsion layer, that contains novel light stabilisers for the azomethine dyes produced during chromogenic development.

It is known to produce colored photographic images by chromogenic development, that is by developing pictorially illuminated silver halide emulsion layers by means of suitable color-forming developer substances—so-called color developers—in the presence of suitable couplers, whereby the oxidation product of the developer substances formed in conformity with the silver image reacts with the coupler to form a dye image. Aromatic compounds containing primary amino groups, especially those of the p-phenylenediamine type, are usually used as color developers.

It is also known that the image dyes produced by chromogenic development undergo certain changes to various extents under the influence of the environmental conditions. This is particularly striking as far as the action of light is concerned. As is known in this case, the magenta dyes fade strongly and the yellow dyes also, to a somewhat smaller extent, while the susceptibility of the cyan dyes produced from phenolic couplers proves to be particularly low in this respect.

There has been no lack of attempts to remedy this deficiency by special measures. It has been possible, especially in the case of the magenta couplers, to achieve improved stability to light by means of light-stabilising additives or special development of the couplers. Mainly suitable as light-stabilising agents are phenolic compounds, that are either mixed with the couplers or combined with the coupler molecules in the form of substituents (DE-B-1 547 803, DE-A-26 17 826, DE-A-29 52 511, JP-N 53 070 822, JP-N 54 070 830, JP-N 54 073 032). The known light stabilisers do not yet, however, satisfy in all respects the requirements set for them.

The invention is based on the object of indicating for photographic recording materials novel light stabilisers, in particular such as are suitable for the improvement of the stability to light of the purple colored or yellow image dyes produced from magenta or yellow couplers respectively.

The present invention provides a color-photographic recording material with at least one silver halide emulsion layer and a coupler allocated thereto, characterised in that it contains in a silver halide emulsion layer or in a neighbouring nonlight-sensitive binder layer a combination of a coupler and a compound of the general Formula I:

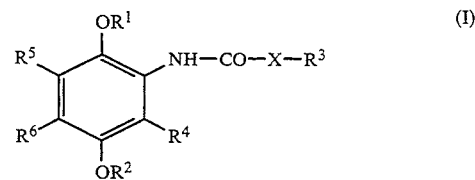

wherein
$R^1$, $R^2$, $R^3$ signify alkyl, aryl;
$R^4$, $R^5$, $R^6$ signify H, alkyl, alkoxy, aryloxy, acyloxy,

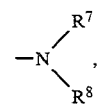

alkoxycarbonyl, carbamoyl;
$R^7$ signifies H, alkyl, aryl;
$R^8$ signifies alkyl, aryl, acyl;
X signifies a single bond, —O—, —NH—.

An alkyl group represented by one of the groups $R^1$ to $R^8$ or contained therein can be straight-chained, branched or cyclic and optionally substituted.

An aryl group represented by one of the groups $R^1$, $R^2$, $R^3$, $R^7$ and $R^8$ or contained therein can optionally be substituted.

Possible substituents of the alkyl or aryl groups are: hydroxy, halogen, —NO$_2$, —CN, carboxy, sulpho, alkoxy, aryloxy, acyloxy, alkylthio, arylthio, acylamino, sulphonamido, acyl, sulphonyl, sulphamoyl.

An acyl group represented by one of the groups $R^1$ to $R^8$ or contained therein as substituent can be derived from an aliphatic or aromatic carboxylic acid, a carbamic acid or a carbonic acid half-ester.

The groups $R^1$ and $R^5$, $R^2$ and $R^4$, $R^2$ and $R^6$ or $R^5$ and $R^6$ can in each case together complete a 5- or 6-membered ring.

In a preferred embodiment of the invention, $R^1$, $R^2$ and $R^3$ represent alkyl and $R^6$ represents H, alkyl or

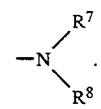

In a further preferred embodiment of the invention, $R^4$ and $R^5$ represent H, alkyl or alkoxy, $R^7$ represents H and $R^8$ represents acyl.

Examples of compounds according to the invention of Formula (I) are

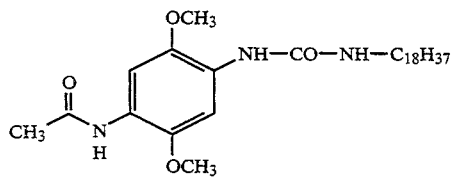

I-1

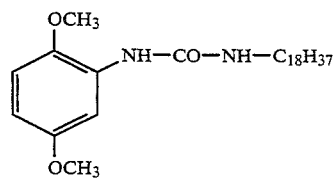

I-2

-continued
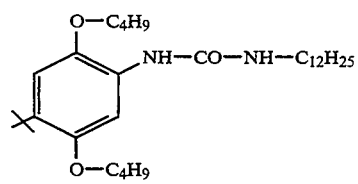  I-3
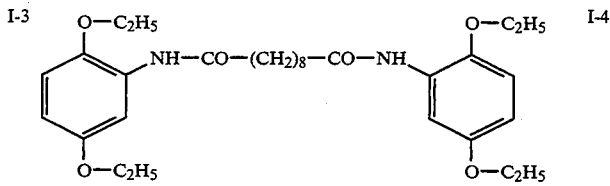  I-4
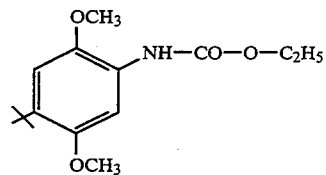  I-5
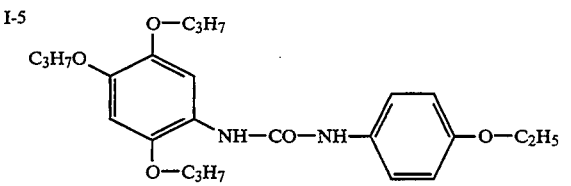  I-6
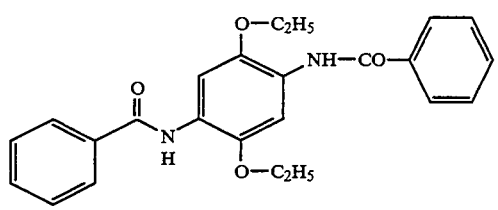  I-7
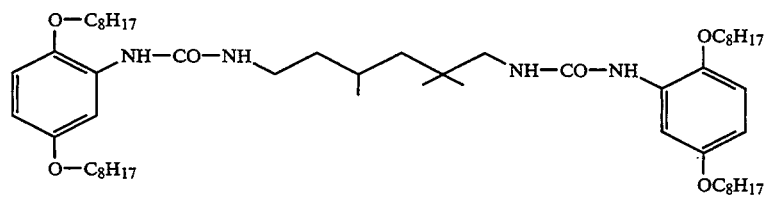  I-8
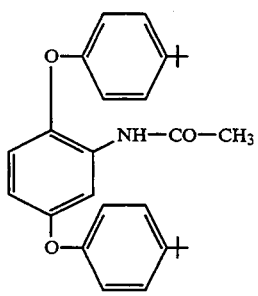  I-9
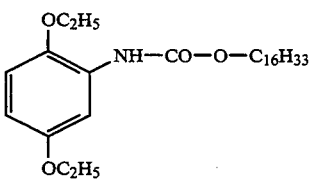  I-10
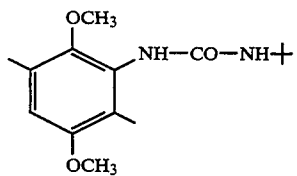  I-11
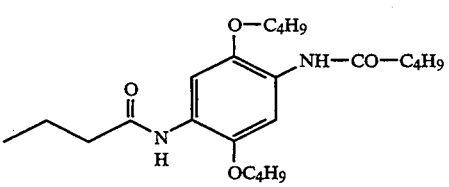  I-12
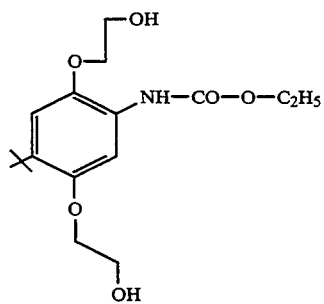  I-13
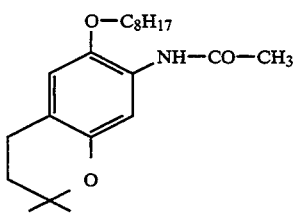  I-14

-continued
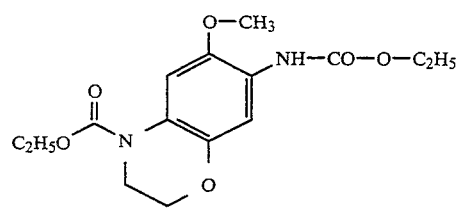
I-15
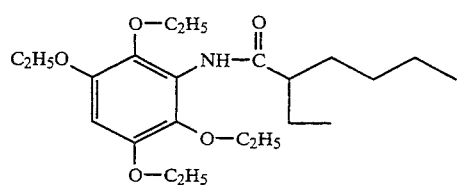
I-16
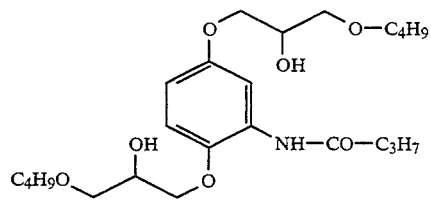
I-17
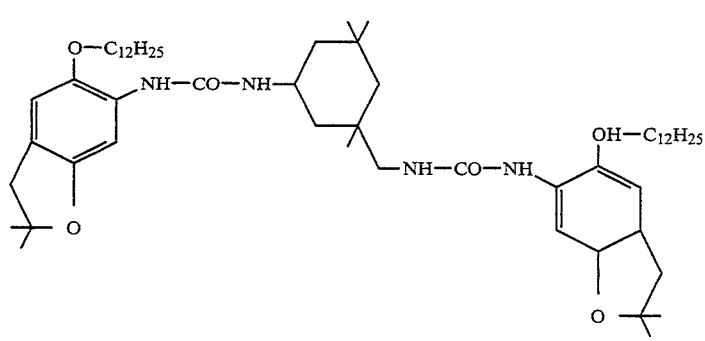
I-18
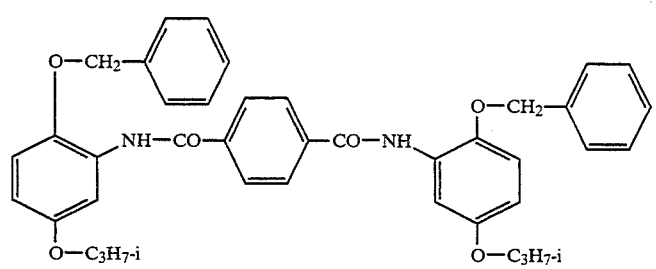
I-19
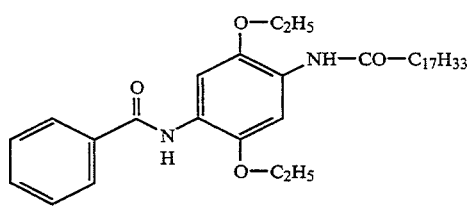
I-20
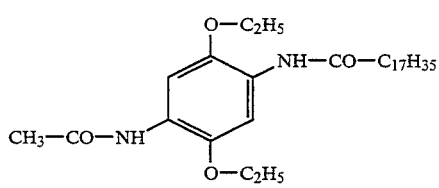
I-21
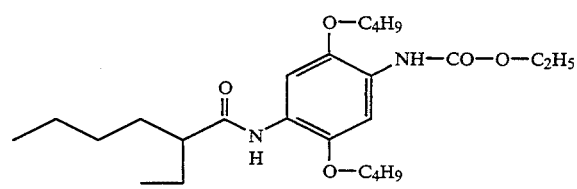
I-22
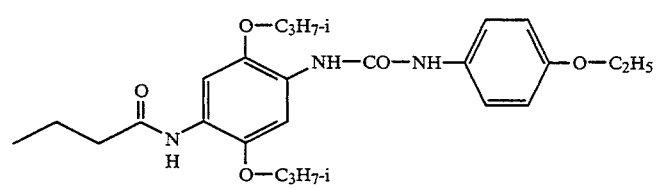
I-23

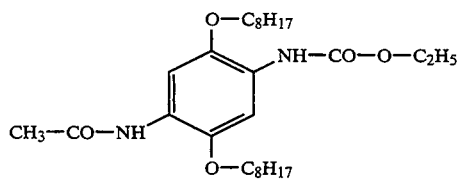 I-24

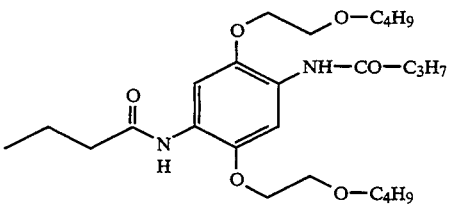 I-25

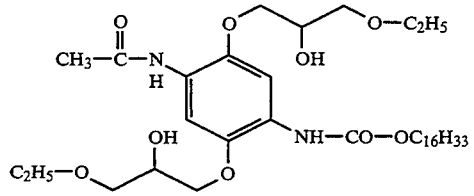 I-26

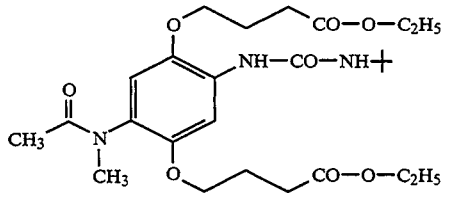 I-27

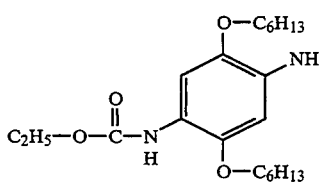 I-28

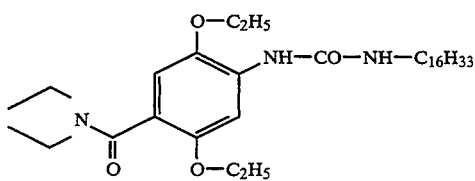 I-29

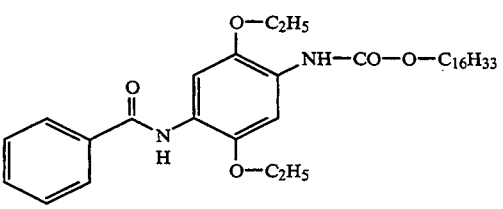 I-30

EXAMPLES OF SYNTHESIS

Synthesis of I-1

100 mmole of 4-acetamino-2,5-dimethoxyaniline are dissolved in 250 ml of $CH_2Cl_2$ and added to 250 ml of a 5% aqueous soda solution. 100 mmole of hexadecyl chloroformate in 100 ml of $CH_2Cl_2$ are slowly added dropwise at room temperature. After 3 hours' agitation the mixture is filtered and the residue recrystallised from ethyl acetate.

Yield: 80% m.p: 129.5°–130° C.

Synthesis of I-2

100 mmole of 2,5-dimethoxyaniline and 100 ml of stearyl isocyanate in 300 ml of acetone are stirred overnight. The precipitate is drawn off by suction and recrystallised from acetone.

Yield: 75% m.p: 120°–121° C.

Synthesis of I-20

100 mmole of 4-benzoylamino-2,5-dimethoxyaniline and 100 mmole of triethylamine are dissolved in 500 ml of $CH_2Cl_2$. 100 mmole of octadecanoyl chloride in 70 ml of $CH_2Cl_2$ are added dropwise at room temperature. After 3 hours' agitation the separated organic phase is reduced to dryness and the residue recrystallised from ethanol.

Yield: 86% m.p: 108°–109° C.

In a further preferred embodiment of the invention the layer containing the compound of Formula I contains in addition at least one compound of one of the Formulae IIA, IIB and IIC

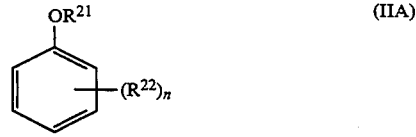 (IIA)

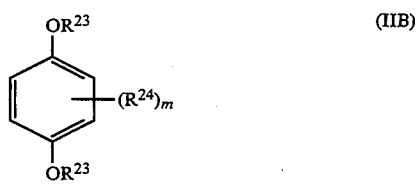 (IIB)

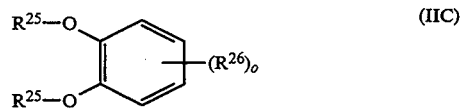 (IIC)

wherein
$R^{21}$ signifies H, alkyl, aryl;
$R^{22}$, $R^{26}$ signify H, OH, —COOH, —$SO_3H$, alkyl, aryl, acyloxy,

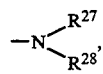

acylamino, sulphonamido, acyl, e.g. carbamoyl or alkoxycarbonyl, sulphonyl, sulphamoyl;
$R^{23}$, $R^{25}$ signify alkyl, aryl;

$R^{24}$ signifies H, —OH, —SO₃H, —COOH, alkyl, aryl, sulphonamido, sulphonyl, sulphamoyl;
$R^{27}$ signifies H, alkyl;
$R^{28}$ signifies alkyl;
n signifies 1–5;
m signifies 0–4;
o signifies 1–4;
wherein several groups $R^{22}$ to $R^{26}$ are the same or different and one group $R^{22}$ or $R^{26}$ that is incapable of being split off under the conditions of chromogenic development is located in the para position to —OR²¹ or to one of the groups —OR²⁵.

An aryl or alkyl group represented by $R^{21}$ to $R^{28}$ can for its part be substituted. Possible substituents are those named for $R^{22}$ as well as alkoxy, aryloxy, alkylthio, arylthio, halogen, —CN and nitro. Groups in the ortho position to each other in Formulae IIA, IIB and IIC can in each case complete a 5- or 6-membered ring.

The groups $R^{21}$ to $R^{28}$ of the compounds of Formulae IIA, IIB and IIC can also be components of a polymer chain.

Examples of compounds according to the invention of Formula II are

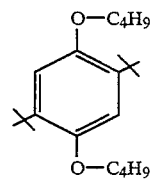
II-1

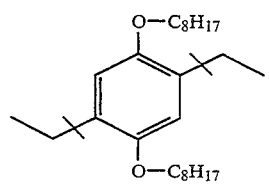
II-2

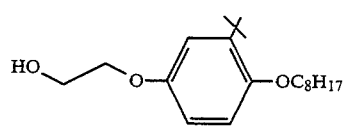
II-3

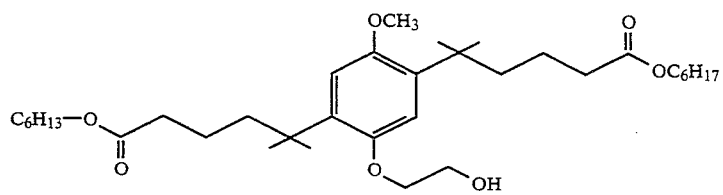
II-4

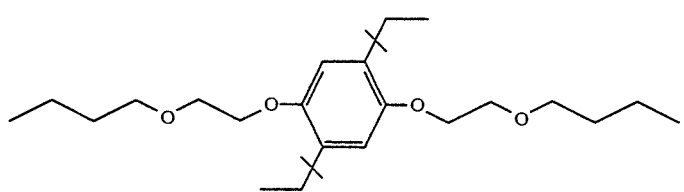
II-5

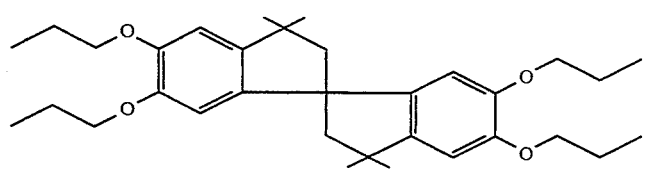
II-6

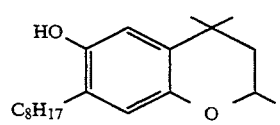
II-7

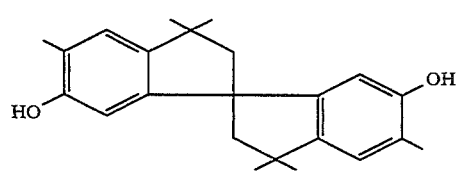
II-8

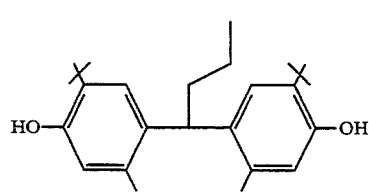
II-9

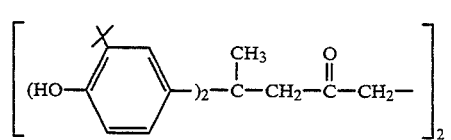
II-10

5,426,022
-continued
II-11
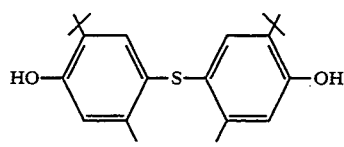
II-12
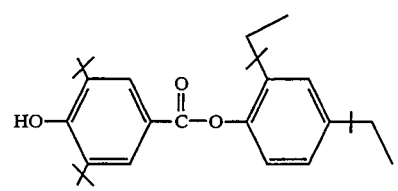
II-13
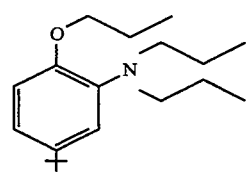
II-14
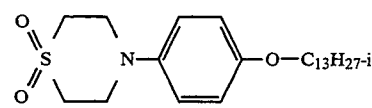
II-15
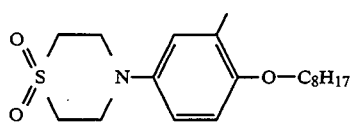
II-16
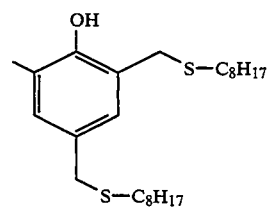
II-17
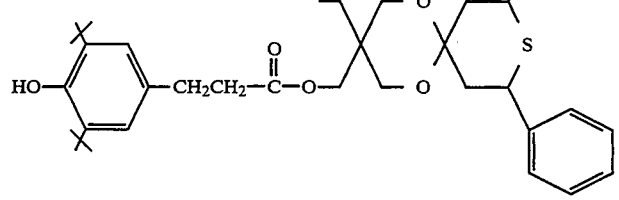
II-18
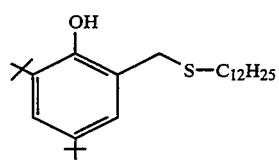
II-19
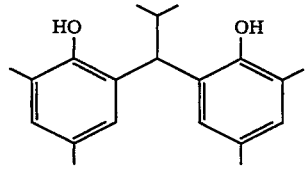
II-20
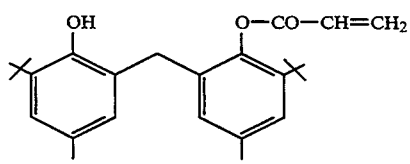
II-21
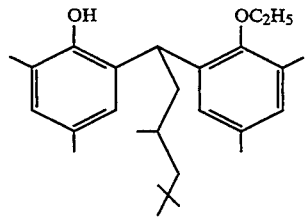
II-22
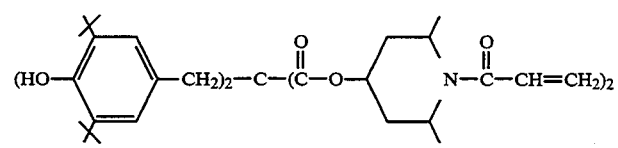
II-23
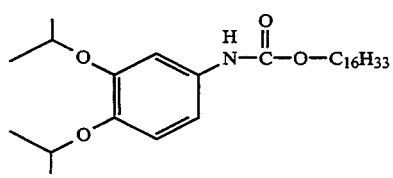
II-24
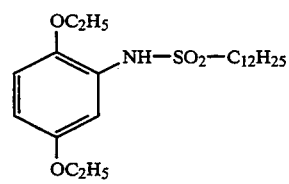

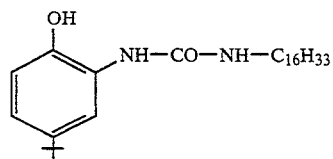 II-25

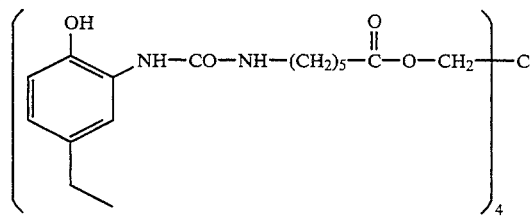 II-26

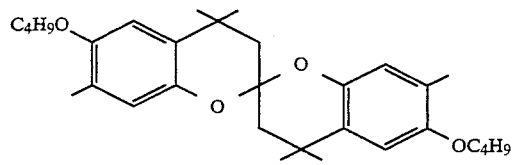 II-27

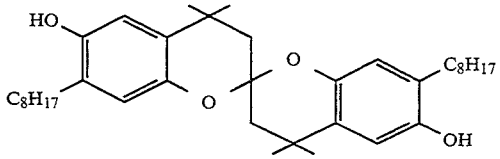 II-28

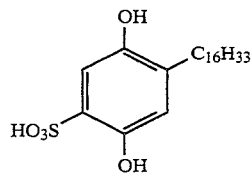 II-30

The color-photographic recording material according to the invention contains at least one light-sensitive silver halide emulsion layer and preferably a sequence of several such light-sensitive silver halide emulsion layers and optionally further auxiliary layers, such as in particular anti-abrasion layers, and, arranged between the light-sensitive layers, nonlight-sensitive binder layers wherein according to the present invention a compound according to the invention of Formula I in combination with a coupler and optionally a compound of Formula II is allocated to at least one of the light-sensitive silver halide emulsion layers present.

The compounds according to the invention act in this connection primarily as light-stabilisers, that is in the presence of the compounds according to the invention the azomethine dyes formed from the coupler during the chromogenic development show a considerably increased stability towards the action of light. Besides that, the compounds according to the invention also in some cases take on the function of an oil-former for the coupler, that is they can be used together with other known oil-formers as coupler solvents. In doing so the compounds according to the invention preferably constitute 10 to 60 wt % of the total amount of oil-formers in the particular layer. The circumstance that other oil-formers are possibly required only in smaller amount has a favourable effect on the layer loading and/or the total layer thickness of the recording materials according to the invention.

The compounds used according to the invention are preferably fed as a solution in aprotic (hydrophobic) solvents, e.g. ethyl acetate, during the introduction into the coating solution for the layer concerned, optionally together with the particular coupler. The introduction is carried out in the usual manner, wherein other auxiliary carried out in the usual manner, wherein other auxiliary solvents and/or high-boiling coupler solvents, so-called oil-formers, can optionally be used. The oil-formers can belong to the following classes of substances among others: carboxylic acid amides, phosphoric acid esters, phosphonic acid esters, sulphones, sulphoxides, sulphonamides, carboxylic acid esters, phenols, polyesters and polyacrylates.

The silver halide present as light-sensitive component in the photographic recording material according to the invention can contain chloride, bromide, iodide or mixtures thereof as halide. For example, the halide portion of at least one layer can consist of 0 to 15 mol % of iodide, 0 to 100 mol % of chloride and 0 to 100 mol % of bromide.

In the case of color-negative and color-reversal films silver bromide iodide emulsions are usually used, and in the case of color-negative and color-reversal paper usually silver chloride bromide emulsions with a high proportion of chloride as far as to pure silver chloride emulsions. Predominantly compact crystals, that are e.g. regular cubic or octahedral or have transitional forms, can be used. Preferably, however, platelike crystals can also be present, whose average ratio of diameter to thickness is preferably at least 5:1, the diameter of a grain being defined as the diameter of a circle with an area corresponding to the projected area of the grain. However, the layers can also have tabular silver halide crystals in which the ratio of diameter to thickness is considerably greater than 5:1, e.g. 12:1 to 30:1.

The silver halide grains can also have a multilayered grain structure with, in the simplest case, an internal and an external zone of the grain (core/shell), wherein the halide composition and/or other modifications, such as dopings, of the individual zones of the grain are different. The average grain size of the emulsions is preferably between 0.2 μm and 2.0 μm and the grain-size distribution can be both homo- or also heterodisperse. A homodisperse grain-size distribution means that 95% of the grains do not deviate by more than ±30% from the average grain size.

The emulsions can also contain, in addition to the silver halide, other silver salts, e.g. organic silver salts, such as silver benzotriazolate or silver behenate.

Two or more types of silver halide emulsions, that are prepared separately, can be used as a mixture.

The emulsions can be chemically and/or spectrally sensitised in the usual manner; they can also be stabilised by suitable additives. Suitable chemical sensitisers, spectral sensitising dyes and stabilisers are described for example in Research Disclosure 17643 (December 1978); reference is made in particular to Chapters III, IV and VI.

The color-photographic recording material according to the invention preferably contains, in addition to the silver halide emulsion layer that contains the combination according to the invention of coupler and compound of Formula I and is sensitive to light of one of the three spectral regions, red, green and blue, other silver halide emulsion layers for the recording of light of the two other spectral regions. For this purpose the light-sensitive layers are spectrally sensitised in known manner by suitable sensitising dyes.

Research Disclosure 17643 (December 1978), Chapter IV contains a survey of the polymethine dyes suitable as spectral sensitisers, their suitable combinations and combinations with supersensitising effect.

The following dyes in particular (arranged by spectral regions) are suitable:

1. as red-sensitisers 9-ethylcarbocyanines with benzothiazole, benzoselenazole or naphthothiazole as basic end groups, that can be substituted in the 5- or 6-position by halogen, methyl, methoxy, carbalkoxy or aryl as well as 9-ethyl-naphthoxathia- or -selenacarbocyanines and 9-ethyl-naphthothiaoxa- or -benzimidazocarbocyanines, provided that the dyes have at least one sulphoalkyl group on the heterocyclic nitrogen.
2. as green-sensitisers 9-ethylcarbocyanines with benzoxazole, naphthoxazole or a benzoxazole and a benzothiazole as basic end groups as well as benzimidazocarbocyanines, that likewise can be further substituted and likewise must contain at least one sulphoalkyl group on the heterocyclic nitrogen.
3. as blue-sensitisers symmetrical or asymmetrical benzimidazo-, oxa-, thia- or selenacyanines with at least one sulphoalkyl group on the heterocyclic nitrogen and optionally further substituents on the aromatic ring, as well as apomerocyanines with a rhodanine group.

Sensitisers can be omitted if for a certain spectral range the intrinsic sensitivity of the silver halide is sufficient, for example the blue-sensitivity of silver bromides.

Each of the light-sensitive layers mentioned can consist of a single layer or also comprise in known manner, e.g. in the so-called double-layer arrangement, two or even more silver halide emulsion component layers (DE-C-1 121 470). In the case of negative films, red-sensitive silver halide emulsion layers are usually arranged closer to the film base than green-sensitive silver halide emulsion layers and the latter closer in turn than blue-sensitive layers, there being in general a nonlight-sensitive yellow filter layer between green-sensitive layers and blue-sensitive layers. Other arrangements are also possible, however, e.g. in the case of color paper. There is arranged, as a rule, between layers of different spectral sensitivity a nonlight-sensitive interlayer, that can in general contain agents for the prevention of inadequate diffusion of developer oxidation products. If several silver halide emulsion layers of the same spectral sensitivity are present, these can be immediately adjacent to each other or so arranged that a light-sensitive layer with another spectral sensitivity is located between them (DE-A-1 958 709, DE-A-2 530 645, DE-A-2 622 922).

Color-photographic recording materials according to the invention usually contain, in spatial and spectral correspondence to the silver halide emulsion layers of different spectral sensitivity, couplers for the production of the different component color images cyan, magenta and yellow.

Spatial correspondence means that the coupler is located in such a spatial relation to the silver halide emulsion layer that an interaction is possible between them that permits a pictorial correspondence between the silver image formed during the development and the color image produced from the coupler. This is achieved as a rule by the coupler being contained in the silver halide emulsion layer itself or in an optionally nonlight-sensitive binder layer adjacent thereto.

Spectral correspondence means that the spectral sensitivity of each of the light-sensitive silver halide emulsion layers and the color of the component color image produced from the spatially corresponding coupler in each case are in a certain relation with each other, each of the spectral sensitivities (red, green, blue) corresponding to another color of the component color image concerned (in general e.g. the colors can, magenta or yellow in that order).

To each of the differently sensitised silver halide emulsion layers, one or even more couplers can be allocated. If several silver halide emulsion layers of the same spectral sensitivity are present, each of them can contain a coupler, and these couplers do not need to be identical. They should merely during the color development produce at least approximately the same color, normally a color that is complementary to the color of the light to which the silver halide emulsion layers concerned are predominantly sensitive.

In preferred embodiments of the present invention, the compounds of Formula I, optionally in combination with compounds of Formula II, are used for the stabilisation of the image dyes produced from yellow couplers or magenta couplers during chromogenic development.

Couplers for the production of the magenta component color image are as a rule couplers of the type of 5-pyrazolone, indazolone or pyrazoloazoles.

In a preferred embodiment, the recording material of the present invention contains together with a compound of Formula I at least one compound of Formula III as magenta coupler

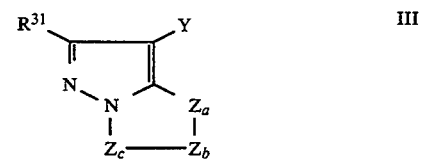

wherein
$R^{31}$ signifies H, alkyl, aralkyl or aryl;
Y signifies H or a group releasable through coupling;

$Z_a$, $Z_b$, $Z_c$ signify an optionally substituted methine group, =N— or —NH—, wherein either the bond $Z_a$—$Z_b$ or the bond $Z_b$—$Z_c$ is a double bond and the other bond in each case is a single bond; couplers of Formula III are known collectively as pyrazoloazole couplers. This means in particular couplers derived from imidazolo[1,2-b]pyrazole, imidazolo[3,4-b]pyrazole, pyrazolo[2,3-b]pyrazole, pyrazolo[3,2-c]-1,2,4-triazole, pyrazolo[2,3-b]-1,2,4-triazole, pyrazolo[2,3-c]-1,2,3-triazole or pyrazolo[2,3-d]tetrazole. The corresponding structures are indicated hereinafter by the Formulae IIIa to IIIg.

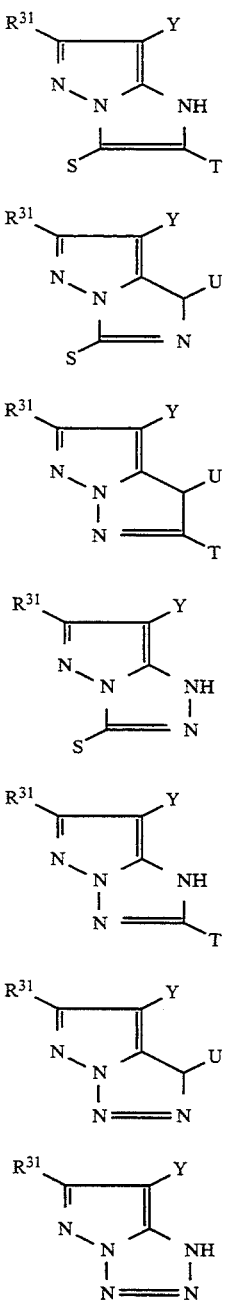

In the general Formulae (IIIa) to (IIIg), the groups $R^{31}$, S, T and U represent hydrogen, cyano, alkyl, aralkyl, aryl, alkoxy, aroxy, alkylthio, arylthio, amino, anilino, acylamino, sulphonamido, alkoxycarbonyl, carbamoyl, sulphamoyl, wherein these groups can be further substituted.

Furthermore Y represents hydrogen or a group releasable during coupling, such as a halogen atom or a preferably cyclic group linked to the coupling position via an oxygen atom, a sulphur atom or a nitrogen atom.

If the releasable group is a cyclic group, the linkage to the coupling position of the coupler molecule can have occurred either directly via an atom that is a component of a ring, e.g. a nitrogen atom, or indirectly via an interposed connecting link. A large number of such releasable groups is known, e.g. as leaving groups of two-equivalent magenta couplers.

Examples of releasable groups linked via oxygen correspond to the Formula

wherein $R^{32}$ represents an acyclic or cyclic organic group, e.g. alkyl, aryl, a heterocyclic group or acyl, that is derived for example from an organic carboxylic or sulphonic acid. In particularly preferred releasable groups of this kind $R^{32}$ signifies an optionally substituted phenyl group.

Examples of releasable groups linked via nitrogen are described in the following German Offenlegungsschriften (DE-A):

5 36 191, 27 03 589, 28 13 522, 33 39 201

In these cases there are often 5-membered heterocyclic rings that are connected via a ring nitrogen atom with the coupling position of the magenta coupler. The heterocyclic rings contain activating groups, e.g. carbonyl or sulphonyl groups or double bonds, often adjacent to the nitrogen atom that provides the bond to the coupler molecule.

If the releasable group is bonded via a sulphur atom to the coupling position of the coupler, it can be the group of a diffusible carbocyclic or heterocyclic mercapto compound, that is able to inhibit the development of silver halide. Such inhibitor groups have often been described as releasable groups bonded at the coupling position of couplers, even purple couplers, e.g. in U.S. Pat. No. 3,227,554. Of the pyrazoloazole couplers of Formulae IIIa to IIIg, those of Formulae IIId and IIIe are preferably used according to the invention. In Formulae IIId and IIIe, at least one of the groups $R^{31}$ and S or at least one of the groups $R^{31}$ and T preferably represents a secondary alkyl or tertiary alkyl group, i.e. a group of the formula

wherein $R^{33}$ and $R^{34}$ represent alkyl and $R^{35}$ represents H or a substituent.

Possible substituents are alkyl, aryl, cycloalkyl, hydroxy, halogen, —COOH, —SO$_3$H, —SO$_2$H, alkoxy, aryloxy, alkylthio, arylthio, nitro, sulphonyl, sulphamoyl, sulphonylamino, acylamino, carbamoyl, acyloxy, alkoxycarbonyl, aryloxycarbamoyl, ureido, carbamoyloxy, alkoxycarbonylamino, aryloxycarbonylamino, alkoxycarbonyloxy and aryloxycarbonyloxy. Preferred substituents are alkyl, sulphonyl, sulphonylamino, sulphamoyl, ureido, acylamino, carbamoyl, alkoxy, aryloxy and alkoxycarbonylamino.
Examples of pyrazoloazole couplers of Formula III are:
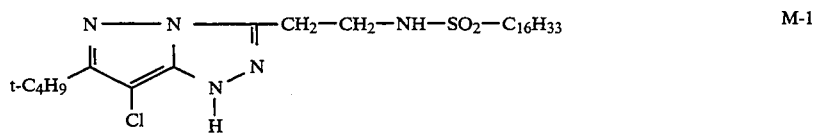
M-1
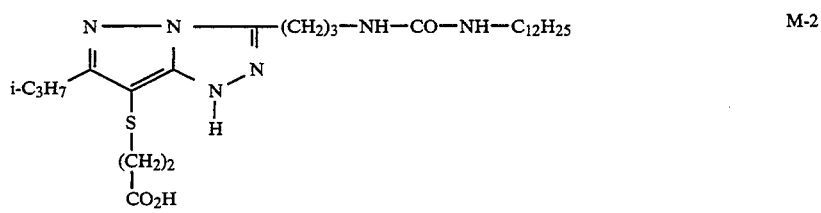
M-2
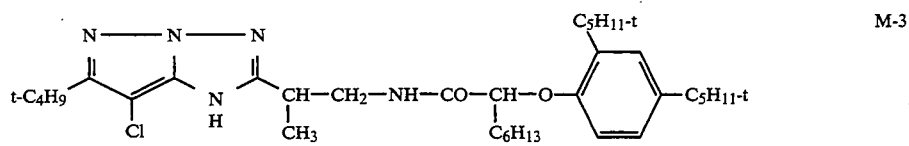
M-3
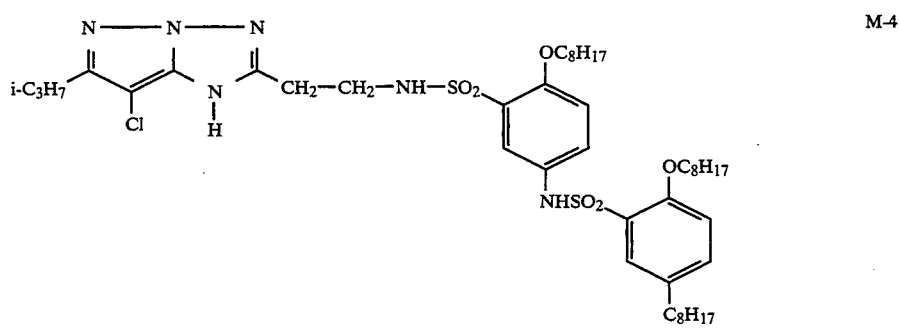
M-4
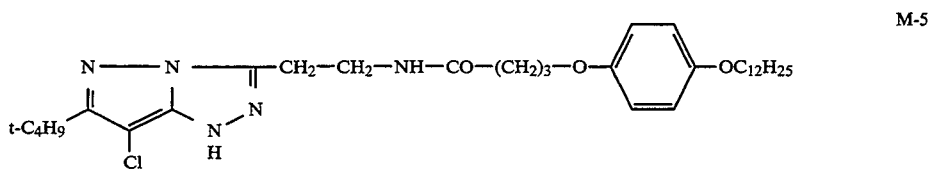
M-5
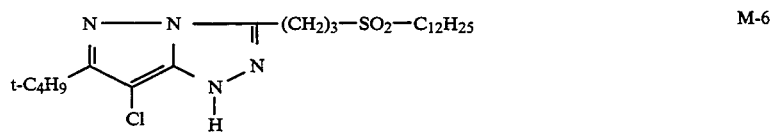
M-6
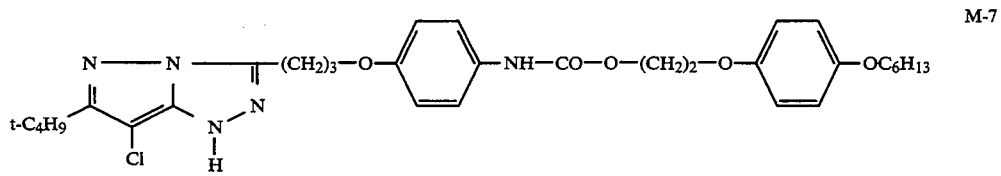
M-7
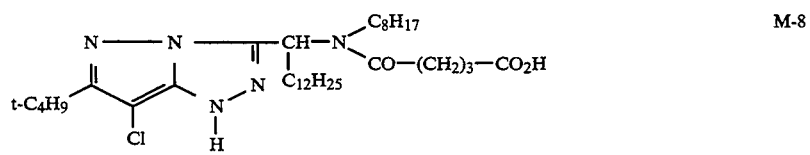
M-8

M-9
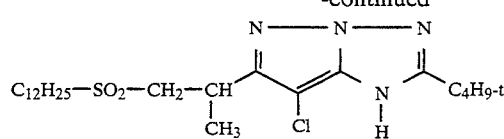
M-10
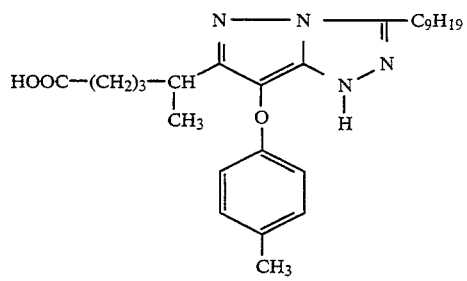
M-11
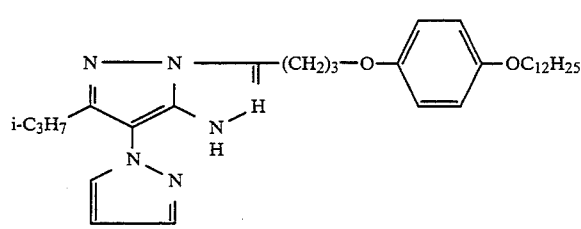
M-12
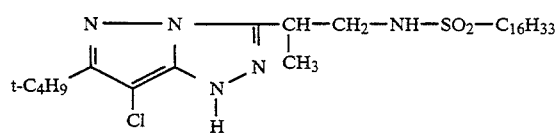
M-13
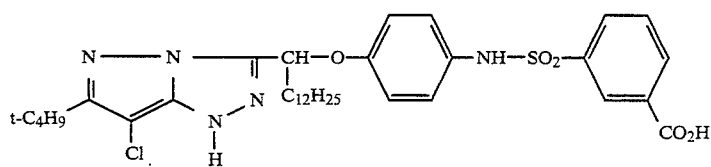
M-14
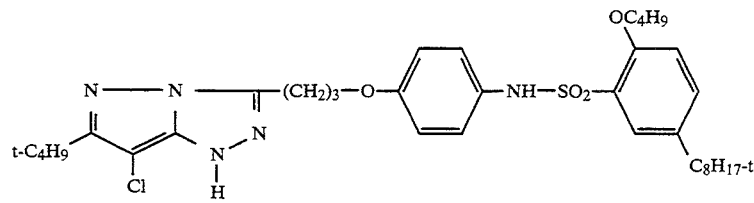
M-15
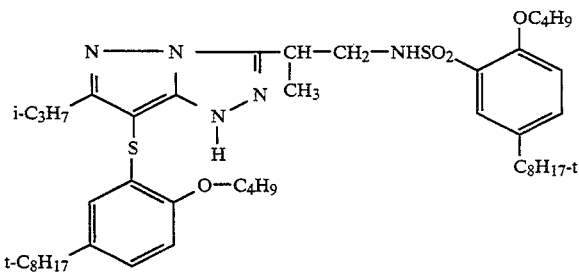
M-16
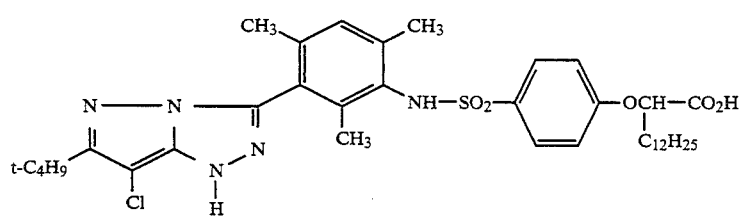

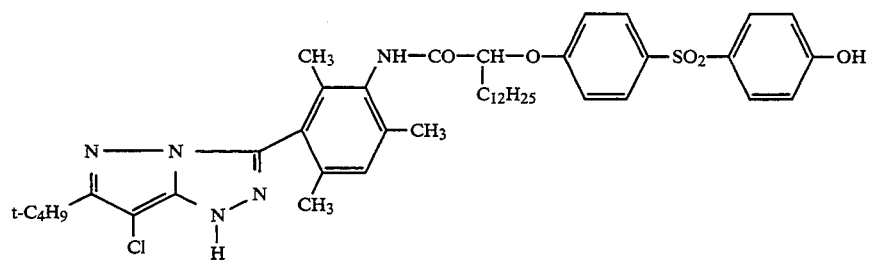
M-17
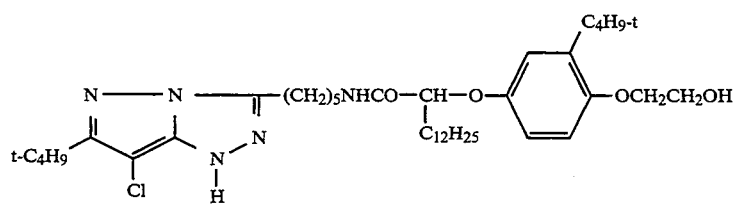
M-18
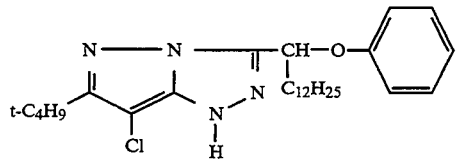
M-19
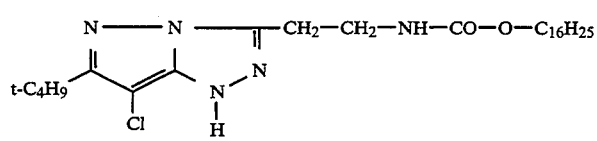
M-20
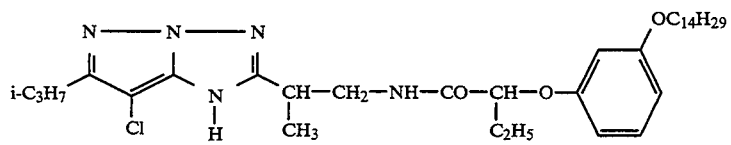
M-21
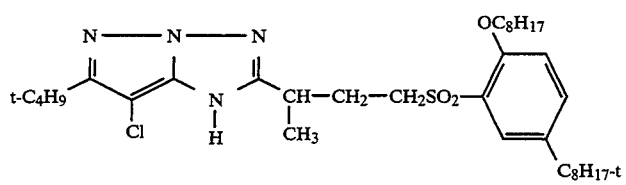
M-22
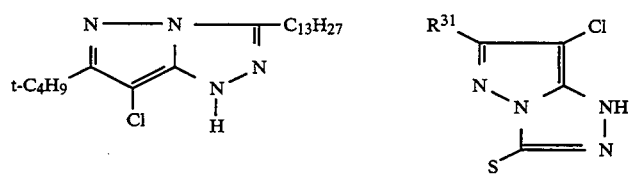
M-23
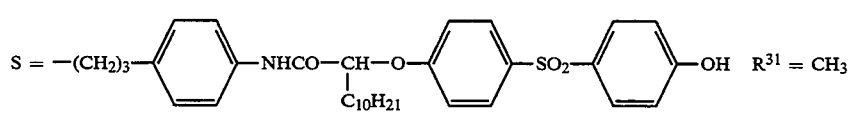
M-24
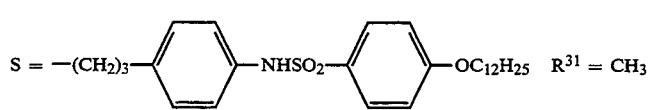
M-25

M-26
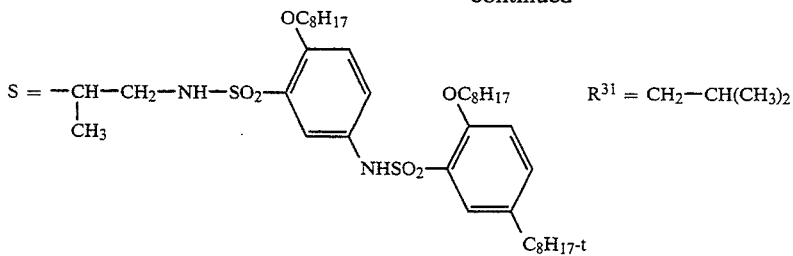
M-27
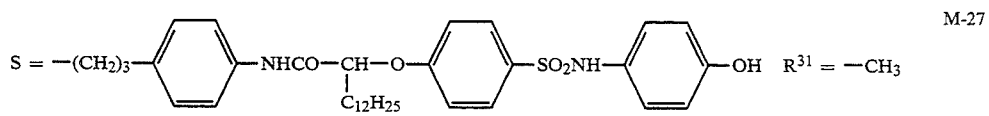
M-28
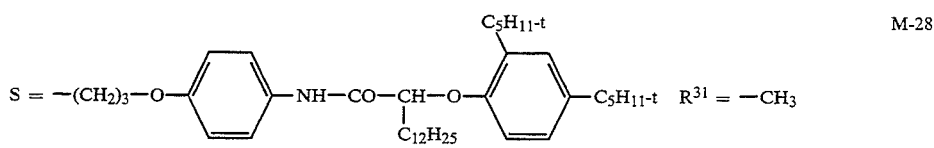
M-29
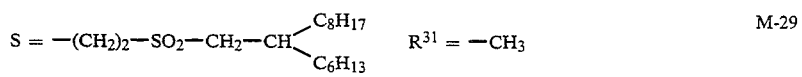
M-30
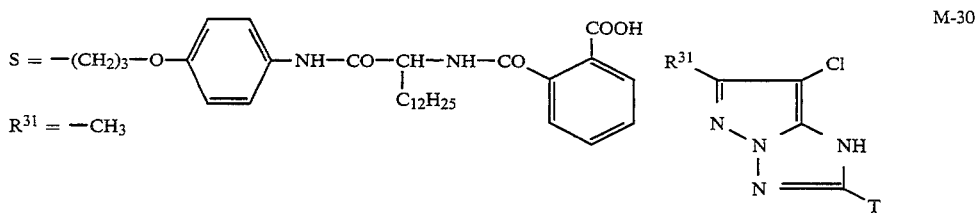
M-31
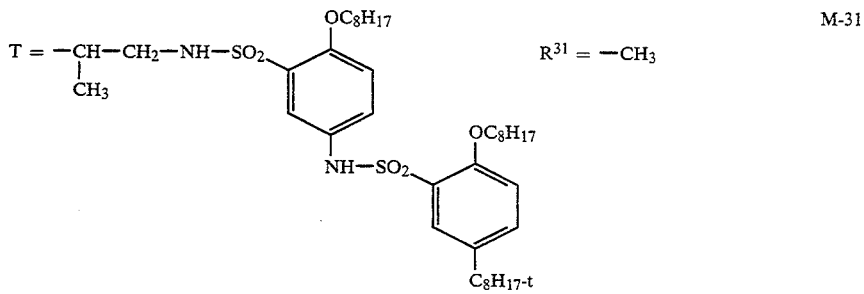
M-32
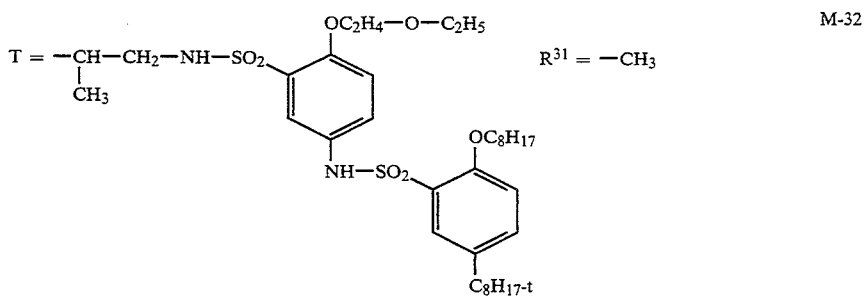
M-33
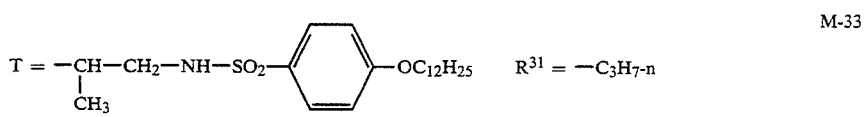
M-34
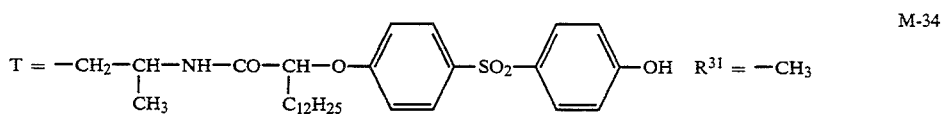

T = —CH₂—CH₂—OCH₃  R³¹ = —CH—CH₂—NH—SO₂— 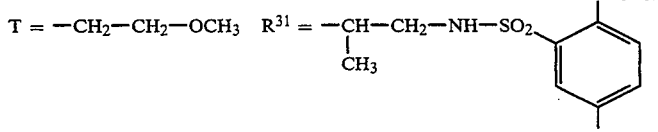  M-34
  |
  CH₃

Couplers for the production of the yellow component color image are as a rule couplers with an open-chain ketomethylene grouping, in particular couplers of the α-acylacetamide type; suitable examples of these are α-benzoylacetanilide couplers and α-pivaloylacetanilide couplers corresponding to Formula IV

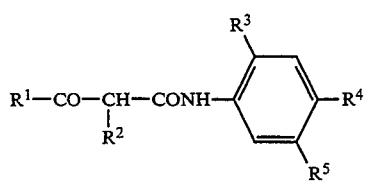 (IV)

wherein
- R¹ signifies an alkyl, cycloalkyl, aryl or heterocyclic group;
- R² signifies a group that can be eliminated under the conditions of chromogenic development;
- R³ signifies chlorine or alkoxy, optionally with linkage to a polymer skeleton;
- R⁴ signifies H, alkyl, alkoxy, sulphamoyl;
- R⁵ signifies acylamino, sulphonamido, alkoxycarbonyl, carbamoyl, sulphamoyl, e.g. a group of the formula —SO₂—NH—CO—alkyl.

R¹ = —C₄H₉-t;  Y-1:

R² = 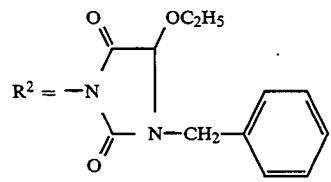

R³ = Cl; R⁴ = H;

R⁵ = —NHCO—CH—O— 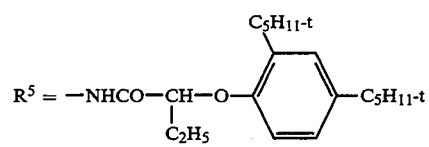
         |
         C₂H₅

R¹ = —C₄H₉-t;  Y-2:

R² = —N 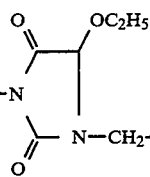 ; R³ = —OC₁₆H₃₃; R⁴ = H;
        |
        COOCH₃

R⁵ = —SO₂NHCH₃
R¹ = —C₄H₉-t;  Y-3:

R² = —O— 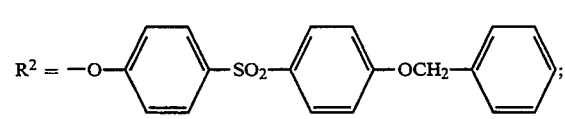 ;

-continued

R³ = Cl
R⁴ = H; R⁵ = —NHSO₂—C₁₆H₃₃
R¹ = —C₄H₉-t;  Y-4:

R² = 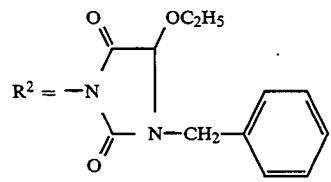 ; R³ = Cl;

R⁴ = H; R⁵ = —COOC₁₂H₂₅
R¹ = —C₄H₉-t;  Y-5:

R² = —O— 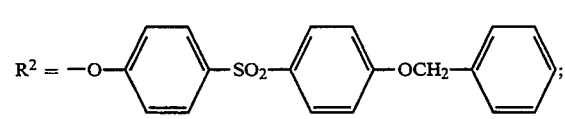 ;

R³ = Cl;
R⁴ = H;

R⁵ = —NHCO(CH₂)₃—O— 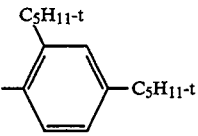

R¹ = —C₄H₉-t;  Y-6:

R² = —O— 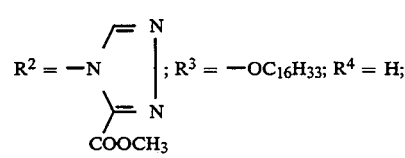 —COOH; R³ = Cl; R⁴ = H;

R⁵ = —NHCO(CH₂)₃O— 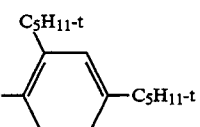

R¹ = —C₄H₉-t;  Y-7:

R² = —O— 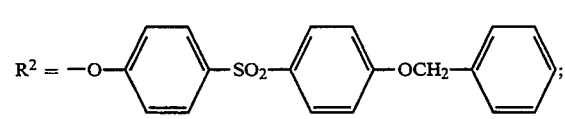 —OH; R³ = Cl;

R⁴ = H; R⁵ = —NHSO₂—C₁₆H₃₃
R¹ = —C₄H₉-t;  Y-8:

-continued
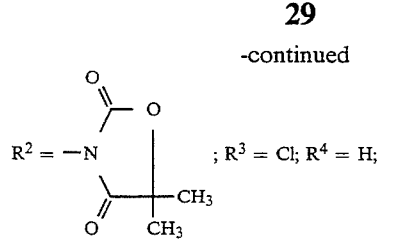
$R^3 = Cl; R^4 = H;$
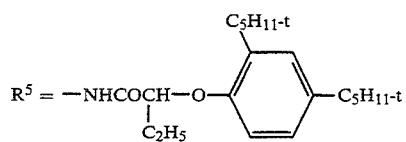
$R^1 = -C_4H_9-t;$
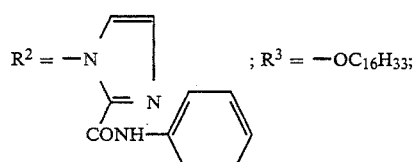
$R^4 = H; R^5 = -SO_2NHCOC_2H_5$
$R^1 = -C_4H_9-t;$
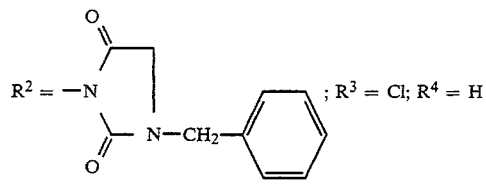
$R^3 = Cl; R^4 = H$
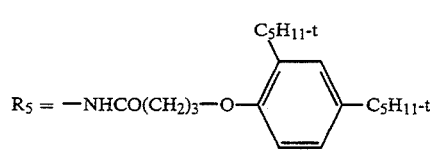
$R^1 = -C_4H_9-t;$
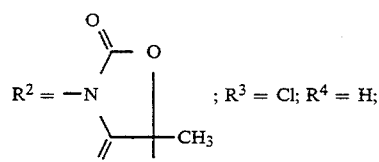
$R^3 = Cl; R^4 = H;$
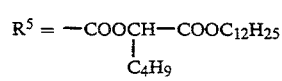
$R^5 = -COOCH-COOC_{12}H_{25}$
         $|$
         $C_4H_9$
$R^1 = -C_4H_9-t;$
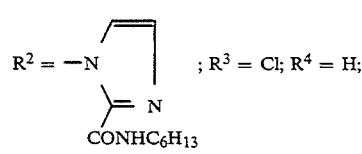
$R^3 = Cl; R^4 = H;$
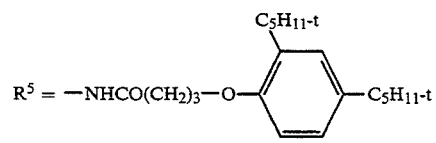
$R^1 = -C_4H_9-t;$
-continued
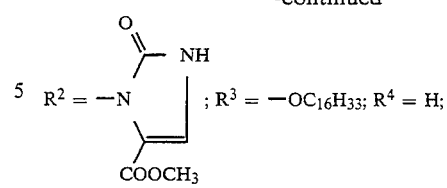
$R^3 = -OC_{16}H_{33}; R^4 = H;$
$R^5 = -SO_2NHCH_3$
$R^1 = -C_4H_9-t;$                                        Y-9:
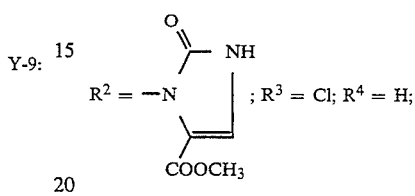
$R^3 = Cl; R^4 = H;$
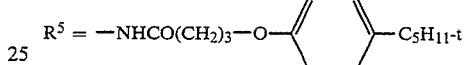
$R^1 = -C_4H_9-t;$                                        Y-10:
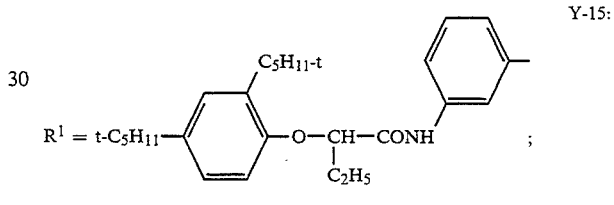
$R^2, R^4, R^5 = H; R^3 = -OCH_3$                        Y-11:
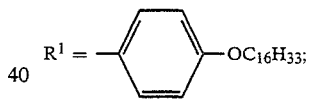                                     Y-12:
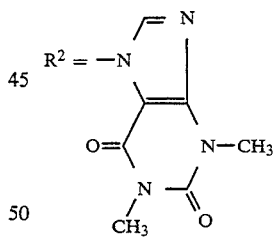
$R^3, R^5 = -OCH_3; R^4 = H$                             Y-13:
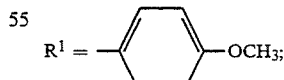                                     Y-14:
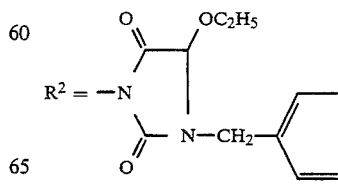                                     Y-15:
Y-16:
Y-17:

-continued

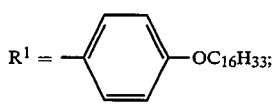

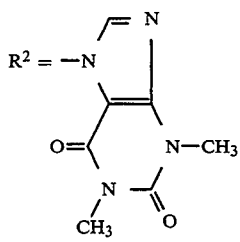

$R^3 = Cl; R^4, R^5 = -OCH_3$

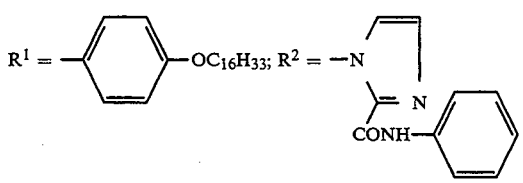

$R^3 = -OCH_3; R^4 = H; R^5 = -SO_2N(CH_3)_2$

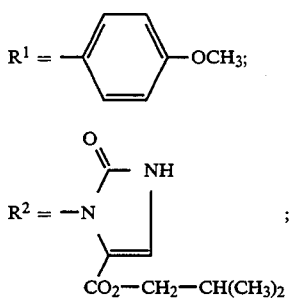

$R^3 = -OCH_3; R^4 = H;$

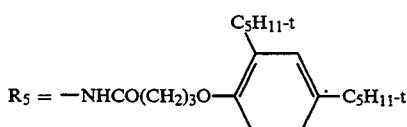

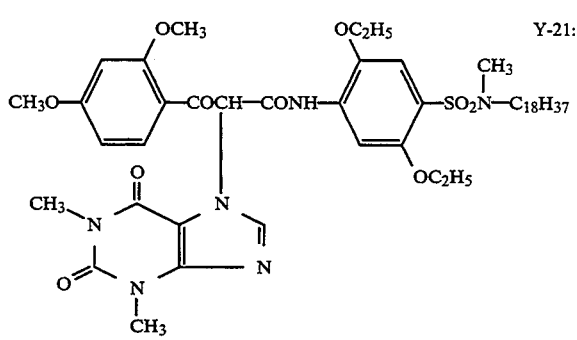

$R^1 = -C_4H_9\text{-t};$

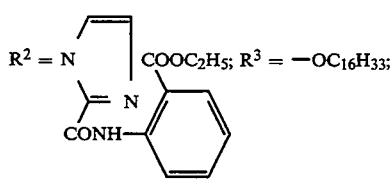

$R^2 = N$ ... $COOC_2H_5; R^3 = -OC_{16}H_{33};$

Y-18: $R^4 = H; R^5 = -SO_2NHCOC_2H_5$ $R^1 = -C_4H_9\text{-t};$

Y-19:

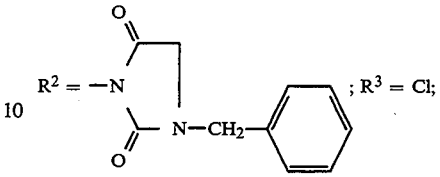 ; $R^3 = Cl;$ $R^3 = H; R^5 = -NHCO-CH(CH_3)CH_2 SO_2C_{12}H_{25};$ $R^1 = -C_4H_9\text{-t};$

Y-20:

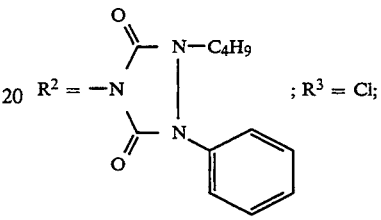 ; $R^3 = Cl;$ $R^4 = H; R^5 = -NHCOCH(CH_3)CH_2SO_2C_{12}H_{25}$

Y-21:

Y-22:

Y-23:

Y-24:

The couplers can be four-equivalent couplers but also two-equivalent couplers. The latter are derived from the four-equivalent couplers by containing in the coupling position a substituent that is released during the coupling. Among the two-equivalent couplers are to be included such as are colorless as well as such as have an intense intrinsic color that during the coupling disappears or is replaced by the color of the image dye produced (masking couplers), but also the white couplers, which yield essentially colorless products on reaction with color developer oxidation products. Furthermore to be included among the two-equivalent couplers are those couplers that contain in the coupling position a group that can be split off and is liberated on reaction with color developer oxidation products and then, either directly or after one or more further groups have been split off from the group primarily split off (e.g. DE-A-27 03 145, DE-A-28 55 697, DE-A-31 05 026, DE-33 19 428), displays a particular desired photographic activity, e.g. as development inhibitor or development accelerator. Examples of such two-equivalent couplers are the known DIR couplers as well as DAR and FAR couplers.

The couplers used, that is the cyan couplers, the magenta couplers, e.g. two-equivalent or four-equivalent magenta couplers of the pyrazolone or pyrazoloazole types, for example of Formulae IId and IIIe, and the yellow couplers, can also be used in polymeric form, e.g. as polymer latex.

High-molecular couplers are described for example in DE-C-1 297 417, DE-A-24 07 569, DE-A-31 48 125, DE-A-32 17 200, DE-A-33 20 079, DE-A-33 24 932, DE-A-33 31 743, DE-A-33 40 376, EP-A-27 284, U.S. Pat. No. 4,080,211. The high-molecular couplers are as a rule produced by polymerisation of ethylenically unsaturated monomeric couplers.

The couplers used can also be such as yield dyes with a low or restricted mobility.

A low or restricted mobility means a mobility of such a degree that that the outlines of the discrete spots of dye formed in the chromogenic development run and become smeared into each other. This degree of mobility is to be distinguished on the One hand from the usual case of complete immobility in photographic layers that is aimed at in conventional photographic recording materials for the couplers and the dyes produced from them, in order to achieve the highest possible sharpness, and on the other hand from the case of the complete mobility of the dyes, which is aimed at for example in color diffusion processes. The last-named dyes usually have available at least one group that isolubilises them in the alkaline medium. The low degree of mobility aimed at according to the invention can be controlled by variation of substituents in order to influence in a purposeful way for example the solubility of the oil-former in the organic medium or the affinity with the binder matrix.

The nonlight-sensitive interlayers arranged as a rule between layers of different spectral sensitivity can contain agents that prevent an undesirable diffusion of developer oxidation products from one light-sensitive layer into another light-sensitive layer with different spectral sensitisation.

Suitable agents, that are also called scavengers or DOP traps, are described in Research Disclosure 17 643 (December 1978), Chapter VII, 17 842 (February 1979) and 18 716 (November 1979), page 650 as well as in EP-A-0 069 070, 0 098 072, 0 124 877 and 0 125 522.

Examples of particularly suitable compounds are:

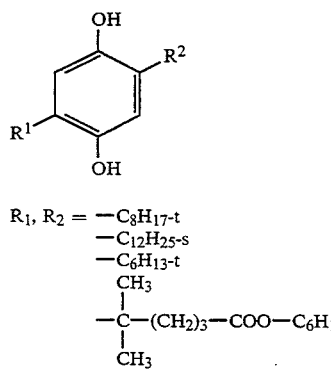

$R_1, R_2 =$ —$C_8H_{17}$-t
—$C_{12}H_{25}$-s
—$C_6H_{13}$-t

—$\overset{CH_3}{\underset{CH_3}{C}}$—$(CH_2)_3$—COO—$C_6H_{13}$

—$C_8H_{17}$-s
—$C_{15}H_{31}$

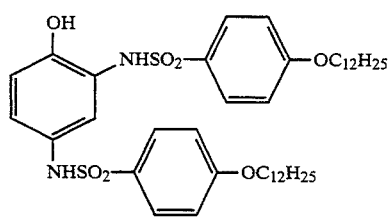

The color-photographic recording material of the present invention can contain, in addition to the components mentioned, other additives, such as antioxidants, dye-stabilising agents and agents for influencing the mechanical and electrostatic properties as well as UV absorbers. Such additional compounds have preferably been used in combination with the compounds according to the invention, i.e. in the same binder layer or in mutually adjacent binder layers.

Additives for improving the stability of dye, coupler and whites as well as for the reduction of chemical fog (Research Disclosure 17 643 (December 1978), Chapter VII) can belong to the following classes of chemical substances: hydroquinones, 6-hydroxychromanes, 5-hydroxycumaranes, spirochromanes, spirondanes, p-alkoxyphenols, sterically hindered phenols, gallic acid derivatives, methylenedioxybenzenes aminophenols sterically hindered amines, derivatives with esterified or etherified phenolic hydroxyl groups and metal complexes.

Compounds that have both a sterically hindered amine partial structure and a sterically hindered phenol partial structure in one molecule (U.S. Pat. No. 4,268,593) are particularly effective for preventing the impairment of yellow color images as a result of the development of heat, moisture and light. For preventing the impairment of magenta color images, in particular their impairment as a result of the action of light, spiroindanes (JP-A-159 644/81) and chromanes, that are di- or monosubstituted by alkoxy groups (JP-A-89 835/80) are particularly effective.

Compounds absorbing UV light should on the one hand protect the image dyes from bleaching by UV-rich daylight and on the other hand, as filter dyes, absorb the UV light in the daylight during the exposure and so improve the color reproduction of a film. Usually, compounds of different structure are used for the two functions. Examples are aryl-substituted benzotriazole compounds (U.S. Pat. No. 3,533,794), 4-thiazolidone compounds (U.S. Pat. No. 3,314,794 and 3,352,681), benzophenone compounds (JP-A-2784/71), cinnamic acid ester compounds (U.S. Pat. No. 3,705,805 and 3,707,375), butadiene compounds (U.S. Pat. No. 4,045,229) or benzoxazole compounds (U.S. Pat. No. 3,700,455).

Examples of particularly suitable compounds are

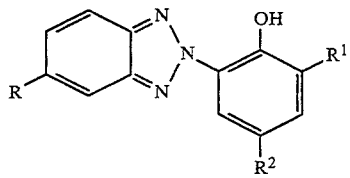

$R, R^1 = H; R^2 = $—$C_4H_9$-t
$R = H; R^1, R^2 = $—$C_4H_9$-t
$R = H; R^1, R^2 = $—$C_5H_{11}$-t
$R = H; R^1 = $—$C_4H_9$-s; $R^2 = $—$C_4H_9$-t
$R = Cl; R^1 = $—$C_4H_9$-t; $R^2 = $—$C_4H_9$-s
$R = Cl; R^1, R^2 = $—$C_4H_9$-t
$R = Cl; R^1 = $—$C_4H_9$-t; $R^2 = $—$CH_2$—$CH_2$—$COOC_8H_{17}$
$R = H; R = $—$C_{12}H_{25}$-i; $R^2 = $—$CH_3$
$R, R^1, R^2 = $—$C_4H_9$-t

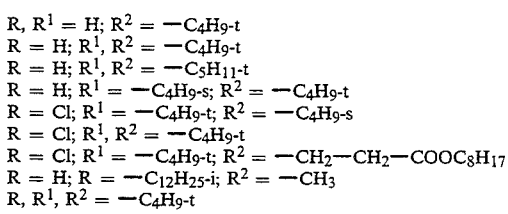

$R^1, R^2 = $—$C_6H_{13}; R^3, R^4 = $—CN

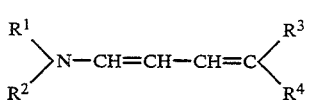

$R^1, R^2 = $—$C_2H_5; R^3 = $—$SO_2$—

$R^4 = $—CO—$OC_8H_{17}$

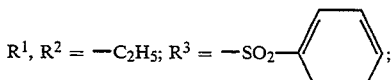

$R^1, R^2 = $—$C_2H_5; R^3 = $—$SO_2$—

$R^4 = $—COO—$C_{12}H_{25}$ $R^1, R^2 = -CH_2=CH-CH_2; R^3, R^4 = -CN$

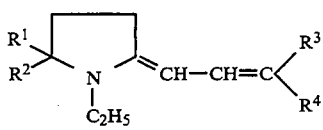

$R^1, R^2 = H; R^3 = -CN; R^4 = -CO-NHC_{12}H_{25}$
$R^1, R^2 = -CH_3; R^3 = -CN; R^4 = -CO-NHC_{12}H_{25}$

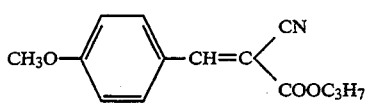

Ultraviolet-absorbing couplers (such as cyan couplers of the α-naphthol type) and ultraviolet-absorbing polymers can also be used. These Ultraviolet absorbers can be fixed by mordanting in a special layer.

For the production of color-photographic images, the color-photographic recording material according to the invention, that contains a coupler and a compound of Formula I allocated to at least one silver halide emulsion layer, is developed with a color developer compound. All developer compounds that have the ability in the form of their oxidation product to react with couplers to form azomethine dyes can be used as color developer compound. Suitable color developer compounds re aromatic compounds of the p-phenylenediamine type containing at least one primary amino group, for example N,N-dialkyl-p-phenylenediamines, such as N,N-diethyl-p-phenylenediamine, 1-(N-ethyl-N-methylsulphonamidoethyl)-3-methyl-p-phenylenediamine, 1-(N-ethyl-N-hydroxyethyl)-3-methyl-p-phenylenediamine, 1-(N-ethyl-N-3-hydroxypropyl)-3-methyl-p-phenylenediamine and 1-(N-ethyl-N-methoxyethyl)-3-methyl-p-phenylenediamine.

Further useable color developers are described for example in J. Amer. Chem. Soc. 73, 3100 (1951) and in G. Haist, Modern Photographic Processing, 1979, John Wiley and Sons, New York, pages 545 ff.

After the colour development the material is usually bleached and fixed. Bleaching and fixing can be carried out separately from each other or also together. The usual compounds can be used as bleaching agents, e.g. $Fe^{3+}$ salts and $Fe^{3+}$ complex salts such as ferricyanides, dichromates, water-soluble cobalt complexes etc. Particularly preferred bleaching agents are iron(III) complexes of aminopolycarboxylic acids, in particular e.g. of ethylenediaminetetraacetic acid, N-hydroxyethylethylenediaminetriacetic acid, alkyliminodicarboxylic acids and of corresponding phosphonic acids. Persulphates also are suitable as bleaching agents.

EXAMPLE 1

A colour-photographic recording material suitable for a rapid-processing process was produced by applying to a film base of paper coated on both sides with polyethylene the following layers in the indicated sequence. The quantity data relate in each case to 1 $m^2$. For the silver halide coat the corresponding amounts of $AgNO_3$ are indicated.

Layer structure Sample 1
  Layer 1: (substrate layer)
    0.2 g gelatine
  Layer 2: (blue-sensitive layer) blue-sensitive silver halide emulsion (99.5 mol % chloride, 0.5 mol % bromide, average grain diameter 0.8 μm) from 0.63 g $AgNO_3$ with
    1.38 g gelatine
    0.95 g yellow coupler Y-22
    0.2 g white coupler XW-1
    0.29 g tricresyl phosphate (TCP)
  Layer 3: (protective coat)
    1.1 g gelatine
    0.06 g 2,5-dioctylhydroquinone
    0.06 g dibutyl phthalate (DBP)
  Layer 4: (green-sensitive layer) green-sensitised silver halide emulsion (99.5 mol % chloride, 0.5 mol % bromide, average grain diameter 0.6 μm) from 0.35 g $AgNO_3$ with
    0.91 g gelatine
    0.31 g magenta coupler M-1
    0.08 g 2,5-dioctylhydroquinone
    0.26 g DBP
    0.03 g TCP
  Layer 5: (UV-protective coat)
    1.15 g gelatine
    0.6 g UV absorber UV-1
    0.045 g 2,5-dioctylhydroquinone
    0.04 g TCP
  Layer 6: (red-sensitive layer) red-sensitised silver halide emulsion (99.5 mol % chloride, 0.5 mol % bromide, average grain diameter 0.5 μm) from
    0.3 g $AgNO_3$ with
    0.75 g gelatine
    0.36 g cyan coupler XC-1
    0.36 g TCP
  Layer 7: (UV-protective coat)
    0.35 g gelatine
    0.15 g UV absorber UV-1
    0.2 g TCP
  Layer 8: (antiabrasion layer)
    0.9 g gelatine
    0.3 g hardener carbamoylpyridinium salt CAS Reg. No. 65411-60-1

In layer 2, the following compound (white coupler XW-1) was used:

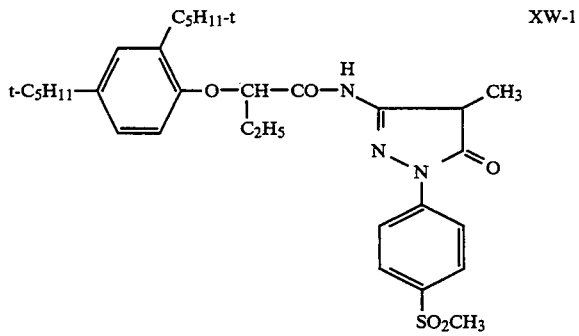

In layers 5 and 7, the following compound (UV absorber UV-1) was used.

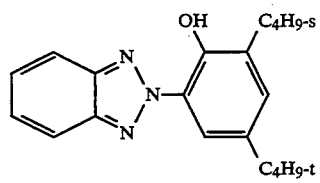

In layer 6 the following cyan coupler (XC-1) was used

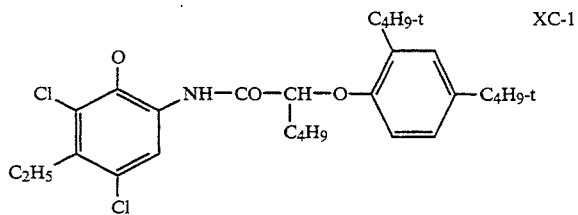

Samples 2 to 13

Samples 2 to 13 were prepared in the same manner as Sample 1, with the difference that to layer 4, that contains the magenta coupler M-1, light stabilisers were added as can be seen from Table 1.

The samples were exposed through a graduated neutral wedge filter and processed in the following manner with the processing baths listed hereinafter.

| a) Colour developer - 45 s - 35° C. | |
|---|---|
| triethanolamine | 9.0 g |
| N,N-diethylhydroxylamine | 4.0 g |
| diethylene glycol | 0.05 g |
| 3-methyl-4-amino-N-ethyl-N-methanesulphonamidoethylaniline sulphate | 5.0 g |
| potassium sulphite | 0.2 g |
| triethylene glycol | 0.05 g |
| potassium carbonate | 22 g |
| potassium hydroxide | 0.4 g |
| ethylenediaminetetraacetic acid, disodium salt | 2.2 g |
| potassium chloride | 2.5 g |
| 1,2-dihydroxybenzene-3,4,6-trisulphonic acid, trisodium salt | 0.3 g |
| made up with water to 1000 ml; pH 10.0 | |
| b) Bleach-fixing bath - 45 s - 35° C. | |
| ammonium thiosulphate | 75 g |
| sodium hydrogen sulphite | 13.5 g |
| ammonium acetate | 2.0 g |
| ethylenediaminetetraacetic acid (iron-ammonium salt) | 57 g |
| ammonia, 25% | 9.5 g |
| made up with glacial acetic acid to 1000 ml; pH 5.5. | |

The samples were exposed to the light of a xenon lamp standardised for daylight and illuminated at $10 \times 10^6$ lx.h; subsequently the percentage density reduction was measured (Table 1).

TABLE 1

| Sample | Coupler | Light stabiliser (amount [g]) | | % density reduction at D = 0.7 | % density reduction at D = 1.5 |
|---|---|---|---|---|---|
| 1 (C) | M-1 | — | — | 80 | 51 |
| 2 (C) | M-1 | II-1 (0.31) | — | 51 | 38 |
| 3 (C) | M-1 | II-9 (0.31) | — | 52 | 42 |
| 4 (I) | M-1 | I-1 (0.31) | — | 28 | 17 |
| 5 (I) | M-1 | I-7 (0.31) | — | 33 | 20 |
| 6 (I) | M-1 | I-10 (0.31) | — | 31 | 19 |
| 7 (I) | M-1 | I-26 (0.31) | — | 29 | 17 |
| 8 (C) | M-1 | II-1 (0.16) | II-9 (0.10) | 49 | 39 |
| 9 (C) | M-1 | II-7 (0.19) | II-13 (0.12) | 56 | 43 |
| 10 (I) | M-1 | I-1 (0.19) | II-1 (0.12) | 26 | 17 |
| 11 (I) | M-1 | I-1 (0.16) | II-3 (0.16) | 24 | 13 |
| 12 (I) | M-1 | I-10 (0.16) | II-10 (0.16) | 27 | 18 |
| 13 (I) | M-1 | I-10 (0.16) | II-14 (0.16) | 23 | 12 |

[(C) = comparison, (I) = according to the invention]

It can be seen from Table 1 that the stability to light of the magenta dye can be clearly improved by use of a compound according to the invention of Formula I. In combination with compounds of Formula II, even synergistic effects are achieved. Compounds of Formula II on their own produce a considerably lower stability to light.

EXAMPLE 2

Samples 14 to 28 were prepared in the same way as Sample 1 of Example 1, with the difference that instead of the magenta coupler M-1, the magenta coupler M-6 (Samples 14–19), the magenta coupler M-15 (Samples 20–24) or the magenta coupler M-23 (Samples 25–28) was used, and that light stabilisers were added to the layer containing the magenta coupler, as can be seen from the following Table 2. Samples 14, 20 and 25 contained no light stabiliser and are used as comparison samples. Samples 14 to 28 were exposed and processed as described in Example 1 and then exposed to the light. The percentage density reduction is indicated in Table 2.

TABLE 2

| Sample | Coupler | Light stabiliser (amount [g]) | | % density reduction at D = 0.7 | % density reduction at D = 1.5 |
|---|---|---|---|---|---|
| 14 (C) | M-6 | — | — | 78 | 44 |
| 15 (C) | M-6 | II-6 (0.31) | — | 54 | 37 |
| 16 (I) | M-6 | I-1 (0.31) | — | 27 | 15 |
| 17 (I) | M-6 | I-13 (0.31) | — | 28 | 17 |
| 18 (I) | M-6 | I-1 (0.20) | II-8 (0.11) | 24 | 13 |
| 19 (I) | M-6 | I-21 (0.13) | II-3 (0.18) | 23 | 13 |
| 20 (C) | M-15 | — | — | 79 | 42 |
| 21 (C) | M-15 | II-2 (0.41) | — | 42 | 31 |
| 22 (I) | M-15 | I-2 (0.41) | — | 23 | 13 |
| 23 (I) | M-15 | I-4 (0.41) | — | 25 | 16 |
| 24 (I) | M-15 | I-29 (0.21) | II-2 (0.20) | 27 | 18 |
| 25 (C) | M-23 | — | — | 88 | 57 |
| 26 (I) | M-23 | I-5 (0.41) | — | 35 | 26 |
| 27 (I) | M-23 | I-6 (0.41) | — | 37 | 29 |
| 28 (I) | M-23 | I-24 (0.25) | II-8 (0.16) | 31 | 23 |

[(C) = comparison, (I) = according to the invention]

It can be seen from Table 2 that the stability to light of the magenta dye is clearly improved by use of a compound according to the invention of Formula I. In combination with compounds of Formula II, even synergistic effects are achieved. Compounds of Formula II on their own produce a considerably lower stability to light.

EXAMPLE 3

Samples 29 to 40 were prepared in the same way as Sample 1 of Example 1, with the difference that in the case of Samples 38 to 40, instead of the yellow coupler Y-22 the yellow coupler Y-23 was used, and that light stabilisers were added, as can be seen from the following Table 3, to the layer containing the yellow couplers Y-22 or Y-23. Samples 1 and 38 contained no light stabiliser and are used as comparison samples. Samples 1 and 29 to 40 were exposed and processed as described in Example 1 and then exposed to daylight ($20 \times 10^6$ lx.h). The percentage density reduction is indicated in Table 3.

TABLE 3

| Sample | Coupler | Light stabiliser (amount [g]) | | % density reduction at D = 0.7 | % density reduction at D = 1.5 |
|---|---|---|---|---|---|
| 1 (C) | Y-22 | — | — | 50 | 69 |
| 29 (C) | Y-22 | II-9 (0.35) | — | 48 | 62 |
| 30 (C) | Y-22 | II-18 (0.35) | — | 44 | 60 |
| 32 (I) | Y-22 | I-2 (0.35) | — | 32 | 45 |

TABLE 3-continued

| Sample | Coupler | Light stabiliser (amount [g]) | | % density reduction at D = 0.7 | % density reduction at D = 1.5 |
|---|---|---|---|---|---|
| 33 (I) | Y-22 | I-29 (0.35) | — | 34 | 49 |
| 34 (C) | Y-22 | II-9 (0.20) | II-18 (0.15) | 44 | 61 |
| 35 (I) | Y-22 | I-2 (0.20) | II-18 (0.15) | 30 | 41 |
| 36 (I) | Y-22 | I-2 (0.15) | II-17 (0.20) | 26 | 35 |
| 37 (I) | Y-22 | I-29 (0.20) | II-22 (0.15) | 27 | 37 |
| 38 (C) | Y-23 | — | — | 36 | 58 |
| 39 (I) | Y-23 | I-8 (0.25) | — | 25 | 40 |
| 40 (I) | Y-23 | I-8 (0.25) | II-12 (0.10) | 20 | 32 |

[(C) = comparison, (I) = according to the invention]

It can be seen from Table 3 that the stability to light of the yellow dye can be clearly improved by use of a compound according to the invention of Formula I. In combination with compounds of Formula II, even synergistic effects are achieved. Compounds of Formula II on their own produce a considerably lower stability to light.

I claim:

1. Color-photographic recording material comprising at least one silver halide emulsion layer to which a color coupler is associated characterized in that it contains in a silver halide emulsion layer or in a nonlight-sensitive binder layer a combination of a coupler and a compound of the general Formula I:

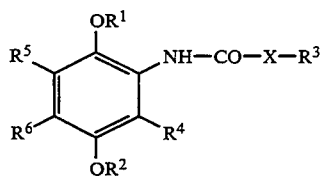
(I)

wherein $R^1$, $R^2$, and $R^3$ are the same or different and are alkyl or aryl;

$R^4$, $R^5$ and $R^6$ are the same or different and are H, alkyl, alkoxy, aryloxy,

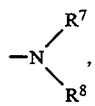

alkoxycarbonyl or carbamoyl;

$R^7$ is H, alkyl or aryl;

$R^8$ is alkyl, aryl or acyl;

X is a single bond, —O— or NH.

2. Recording material according to claim 1, wherein the layer containing the compound of Formula I additionally contains at least one compound selected from the group consisting of one of the Formulae IIA, IIB and IIC

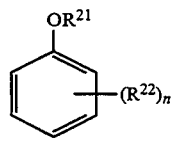
(IIA)

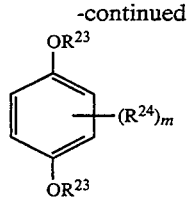
(IIB)

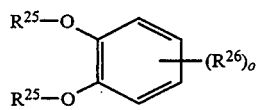
(IIC)

wherein $R^{21}$ is H, alkyl or aryl;

$R^{22}$ and $R^{26}$ are the same or different and are H, OH, —COOH, —SO$_3$H, alkyl, aryl, acyloxy

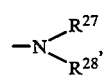

acylamino sulphonamido, acyl, sulphonyl or sulphamoyl;

$R^{23}$ and $R^{25}$ are the same or different and are alkyl or aryl;

$R^{24}$ is H, —OH, —SO$_3$H, —COOH, alkyl, aryl, sulphonamido, sulphonyl or sulphamoyl;

$R^{27}$ is H, or alkyl;

$R^{28}$ is alkyl;

n is an integer from 1–5;

m is an integer from 0–4;

o is an integer from 1–4;

wherein one group $R^{22}$ or $R^{26}$ is selected from the group consisting of —OH, —COOH, —SO$_3$H, alkyl, aryl acyloxy

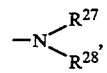

acylamino sulphonamido, acyl, sulphonyl and sulphamoyl; and is located in the para position to —OR$^{21}$ or to one of the groups —OR$^{25}$.

3. Recording material according to claim 1, wherein the compound of Formula I is contained in a layer containing a magenta coupler.

4. Recording material according to claim 3, wherein the magenta coupler corresponds to the Formulae IIId or IIIe

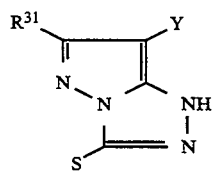
(IIId)

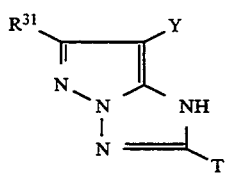
(IIIe)

wherein $R^{31}$, and T are the same or different and are H, cyano, alkyl, aralkyl, aryl, alkoxy, aryloxy, alkylthio, arylthio, amino, anilino, acylamino, sulphonamido, alkoxycarbonyl, carbamoyl or sulphamoyl;

Y is H or a group that can be liberated under the conditions of chromogenic development.

5. Recording material according to claim 4, wherein Formulae IIId or IIIe at least one of the groups $R^{31}$, S and T represents secondary alkyl or tertiary alkyl.

6. Recording material according to claim 1, wherein the compound of Formula I is contained in at least one layer containing a yellow coupler of Formula IV:

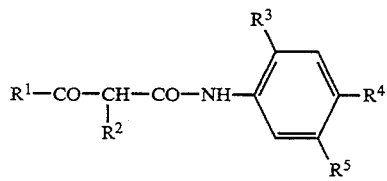

wherein $R^1$ is alkyl, cycloalkyl, aryl, or a heterocyclic group;

$R^2$ is a group that can be eliminated under the conditions of chromogenic development;

$R^3$ is chlorine or alkoxy;

$R^4$ is H, alkyl, alkoxy or sulphamoyl;

$R^5$ is acylamino, suphonamido, alkoxycarbonyl, carbamoyl or sulphamoyl.

7. The recording material as claimed in claim 2, wherein $R^{22}$ and $R^{26}$ are the same or different and are a carbamoyl or alkoxycarbonyl.

8. The recording material as claimed in claim 1, wherein $R^1$, $R^2$ and $R^3$ are the same or different and represent alkyl, and $R^6$ represents hydrogen, alkyl or

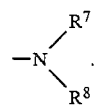

9. The recording materials claimed in claim 1, wherein $R^4$ and $R^5$ are the same or different and represent hydrogen, alkyl or alkoxy, $R^7$ represents hydrogen and $R^8$ represents acyl.

10. The recording materials claimed in claim 8, wherein $R^4$ and $R^5$ are the same or different and represent hydrogen, alkyl or alkoxy, $R^7$ represents hydrogen and $R^8$ represents acyl.

* * * * *